United States Patent [19]

Boschman et al.

[11] 3,959,473

[45] May 25, 1976

[54] QUINOLINE DERIVATIVES HAVING PHARMACOLOGICAL EFFECTS

[75] Inventors: Theodorus Antonius Cornelis Boschman; Jacob Gerard Korsloot, both of Weesp, Netherlands

[73] Assignee: U.S. Philips Corporation, New York, N.Y.

[22] Filed: Dec. 4, 1974

[21] Appl. No.: 529,291

Related U.S. Application Data

[62] Division of Ser. No. 329,692, Feb. 5, 1973, Pat. No. 3,865,832.

[30] Foreign Application Priority Data

Feb. 9, 1972 Netherlands...................... 7201675
Nov. 14, 1972 Netherlands...................... 7215366

[52] U.S. Cl. .............................................. 424/258

[51] Int. Cl.² ........................................ A61K 31/47
[58] Field of Search.................. 260/287 R; 424/258

[56] References Cited
UNITED STATES PATENTS 3,178,348   4/1966   Bickerton...................... 260/287 R

FOREIGN PATENTS OR APPLICATIONS 1,240,316   7/1971   United Kingdom................. 260/287

*Primary Examiner*—Sam Rosen
*Attorney, Agent, or Firm*—Frank R. Trifari; Norman N. Spain

[57] ABSTRACT

Diuretic compositions containing novel carbonylic quinoline derivatives and methods of treating patients suffering from various edemas with these compositions.

36 Claims, No Drawings

QUINOLINE DERIVATIVES HAVING PHARMACOLOGICAL EFFECTS

This is a division of application Ser. No. 329,692, filed Feb. 5, 1973, and now U.S. Pat. No. 3,865,832.

The invention relates to novel quinoline derivatives having pharmacological effects.

A large number of quinoline derivatives are described, inter alia, in Belgian Pat. No. 725.787. Antibacterial and coccidiostatic properties of the known compounds have been described.

It was found that the compounds of the formula I have a strong diuretic and saluretic effect.

In formula I the symbols have the following meanings:

$R_1$ is either a group

where $R_5$ is an alkoxy or dialkylaminoalkoxy group, an alkoxyalkyloxy, alkenyloxy, cycloalkoxy or cycloalkylalkoxy group containing at most 4 C atoms, but if $R_3$ denotes a halogen atom or a $CF_3$ group, at most 6 C atoms, a hydroxy group, an amino group, a hydrogen atom or an alkyl group containing at most 3 C atoms, or a group $CHR_4OR_6$, where $R_6$ is a hydrogen atom or an acyl group containing from 2 to 4 C atoms and $R_4$ is a hydrogen atom or an alkyl group containing at most 3 C atoms, or an alkyl group containing at most 4 C atoms;

$R_2$ represents either a group $(CH_2)_n OR_7$, where $R_7$ is a hydrogen atom, an alkyl, cycloalkyl, alkenyl, cycloalkenyl, alkoxyalkyl or tetrahydrofuranylalkyl group containing at most 6 C atoms, an acyl group containing from 2 to 4 C atoms, a phenylalkyl group containing up to 8 C atoms or a dialkylaminoalkyl group, whilst $n$ is 1 or 2, or a group $(CH_2)_n S(O)_m$—$R_8$, where $R_8$ represents an alkyl group containing from 1 to 3 C atoms, $m$ is 0, 1 or 2 and $n$ is 1 or 2;

$R_3$ is a hydrogen atom or a halogen atom, an alkyl or alkoxy group containing at most 4 C atoms, a trifluoromethyl group, a nitro or amino group, an acylamino group containing up to 4 C atoms, a cyano or a hydroxy group;

and R represents a hydroxy or mercapto group, an alkoxy or alkylthio group containing at most 3 C atoms or, if $R_3$ represents a halogen atom or a trifluoromethyl group, a chlorine or bromine atom.

The said compounds include the alkali metal salts of the carboxyl group $R_1$ and the acid addition salts formed with pharmaceutically acceptable acids. The term "alk(en)yl (oxy) groups" denotes both straight-chain and branched-chain groups.

Because the compounds contain an asymmetric carbon atom, the formula 1 denotes both racemates and enantiomers. The compounds in which R represents a hydroxy group or a mercapto group are tautomeric with the compounds of the formula 1a in which X represents an oxygen atom or a sulphur atom. The equilibrium is greatly shifted towards the structure of formula 1a. Hence compounds of the formula 1a also are considered as falling within the scope of the invention.

The fact that compounds of the formula I have diuretic properties is the more surprising because the known compounds have no diuretic effects.

The following Table shows the result of a diuretic test in which the effect of compounds according to the invention (formulae 2a and 2b) were compared with those of a closely related compound described in the aforementioned Belgian Patent Specification (formula 3):

| compound of the formula | dose mg/kg oral | increase in volume of urine in per cent |
|---|---|---|
| 2a | 12.5 | 130 |
| 2b | 5 | 110 |
| 3 | 50 | 10 |

If in the compound of the formula 2a a chlorine atom is introduced at the position 10, a compound is obtained that is about 100 times more potent.

The compounds of the formula I have a strong diuretic effect showing a high ceiling. Unlike the commonly used diuretic furosemide (4-chloro-5-sulfamoyl-N-(furyl-2-methyl) anthranilic acid) the compounds have a dose-effect relation which varies very gradually. As a result, the compounds may readily be used and in spite of individual differences in sensitivity between patients they may be administered without the risk of excessive or insufficient effect of the dose administered.

The diuretic effect is accompanied by a saluretic effect which mainly shows itself as a strong increase in the excretion of sodium ions, whereas the increase of the excretion of potassium ions is much smaller.

In renally hypertensive rats the compounds cause a fall in blood pressure after repeated administration.

The toxicity of the compounds is very small. For example, in the mouse on oral administration the compound of the formula 2a has a $LD_{50}$ of 4,080 mg/kg, the compound of formula 2b a $LD_{50}$ of > 1,000 mg/kg. Even after repeated administration no influence on the blood sugar content is found.

The compounds may be used for treating hypertension, cardiac asthma, decompensation of the heart, pulmonary edema, hepatic edema with ascites, nephrogenous edema, cardiac edema, pregnancy edema, lymphatic, edema, iodopathic edema, edema in adiposis, post-traumatic edema, medicamentous edema, edema in malignant diseases, premenstrual tension, nephrotic syndrome, gestational toxicosis, barbiturate intoxication, inhibition of lactation and renal and central diabetes insipidus.

The doses in which, the frequency at which and the route by which the compounds are administrated depend upon the nature and the seriousness of the diseases for the treatment of which they are used. In general a daily dose of from 0.5 mg to 200 mg will be sufficient.

The compounds of the formula 1 in which R represents a hydroxy group, $R_1$ an alkoxycarbonyl, alkoxyalkoxycarbonyl, carboxyl, alkylcarbonyl or hydroxymethyl group, $R_2$ is an alkoxyalkyl or an alkoxyalkoxyalkyl group and $R_3$ is a hydrogen atom, a halogen atom, a trifluoromethyl group or a nitro group, have particularly strong diuretic effects. Among these compounds particularly, those in which $R_3$ represents a halogen atom have are particularly potent.

The diuretic effect of the compounds was determined in the test arrangement described by Lipschitz, Hadidian and Kerpcsar, J. Pharm. exptl. Therap. 79, 97–110 (1943), with a few small modifications. The compounds to be tested were suspended in an aqueous 1 per cent by weight solution of tragacanth in water and orally administered to male rats (weight between 100 g and 200 g) which were fasted for 18 hours. Immediately after th administration of the substance they were orally given 2,5 ml of physiological salt solution per 100 g of body weight. The animals were put in metabolism cages in which urine and faeces could be collected separately. The urine was collected in graduated vessels, and readings of the volume were taken 2½ hours and 5 hours after administration. The amounts of Na ions, K ions and Cl ions in the urine obtained after 5 hours were determined. The urine volumes and the electrolyte concentrations of the animals treated with the compounds were compared with those of control animals.

The compounds of the formula 1 can be obtained by known methods. Accordingly the invention also relates to a method of preparing novel quinoline derivatives which is characterized in that compounds of the formula 1, alkali metal salts, acid addition salts and tautomers thereof are prepared by methods known for the preparation of such compounds and by analogous methods.

For example, compounds of the formula 1 in which R is an OH group are obtainable in intramolecular condensation of a compound of the formula 4 or a tautomer thereof. In this formula the symbols $R'_1$ to $R'_3$ have the same meanings also have $R_1$ to $R_3$ in the formula 1, however, hydroxy groups and amino groups now are protected by benzyl, benzyloxycarbonyl, acyl or alkoxycarbonyl groups. $R_9$ denotes the same group als $R'_1$ when $R'_1$ represents a carboxyl group or an esterified carbonyl group, but in all other cases it may also represent a halogencarbonyl group or a group

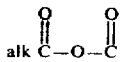

where alk is a lower alkyl group, for example a methyl group or an ethyl group.

The reaction is carried out at elevated temperatures up to at most about 250°C. The reaction may proceed in the melt or in a solution. In the latter case a high-boiling-point solvent, such as diphenyl, diphenyl ether, mineral oils and the like, may be used, or a condensing agent, such as polyphosphoric acid or an ester thereof, phosphorus oxychloride ($POCl_3$), phosphorus pentoxide, quinoline, aluminium chloride and the like, and a solvent may be used. In some cases the condensing agent may also serve as a solvent. After the condensation reaction the protected hydroxy and amino groups in $R'_1$ $R'_3$ can be converted into free amino and hydroxy groups by acid or alkaline hydrolysis. Protective benzyl and benzyloxycarbonyl groups may also be removed by hydrogenolysis, for example with Pt or Pd/C and hydrogen under a slightly increased pressure, for example 1.1 atmospheres.

Compounds of the formula 4 are obtainable by condensing a compound of the formula 5, for example in ethanol, with a compound of the formula 6.

The reaction product need not be isolated, but may be converted into compounds of the formula 1, for example, by adding a high-boiling-point solvent and raising the temperature.

The amines of the formula 5 are usually obtained by reducing the corresponding nitrocompounds, for example with Pd/C and hydrogen.

The compounds of the formula 1 in which R represents a hydroxy group may also be obtained by intramolecularly condensing a compound of the formula 7 or a tautomer thereof in which $R_{10}$ represents a carboxyl group or an esterified carboxyl group. This reaction may be carried out in an inert solvent such, for example, as diethyl ether and a base such, for example, as an alcoholate at temperatures between room temperature and the boiling point of the mixture. After the condensation reaction free amino groups and hydroxy groups are obtainable from the protected hydroxy groups and amino groups in $R'_1$ to $R'_3$ by hydrolysis or hydrogenolysis. The compounds of the formula 7 may be obtained by reacting a compound of the formula 8 with a compound of the formula 9 in an inert solvent, such as ethanol, with heating.

Another method of preparing compounds of the formula 1 is that in which a compound of the formula 10 or a tautomer thereof is intramolecularly condensed. The reaction is carried out in an inert solvent, such as for example dioxan, in the presence of a catalytic amount of a base, for example NaOH or KOH. The reaction is performed at temperatures between room temperature and about 100°C. After the condensation reaction the protected hydroxy groups and amino groups in the substituents $R'_1$ to $R'_3$ are converted into free amino groups and hydroxy groups by hydrolysis or hydrogenolysis. The compounds of the formula 10 are obtainable by reacting a compound of the formula 11 with a compound of the formula 12 or a tautomer thereof, for example in dioxan, using a base as a catalyst. Compounds of the formula 11 are obtained by reacting the corresponding anthranilic acid derivitative with phosgene.

Since compounds of the formula 10 are converted into compounds of the formula 1 under the same conditions under which they are obtained from compounds of the formula 11, the starting substances of the formula 10 can be prepared in situ.

The compounds of the formula 1 in which R represents a hydroxy group are also obtainable by ring closure of a compound of the formula 13 or a tautomer thereof in which Hal represents a halogen atom. The reaction is carried out in an inert solvent such as, for example, water, alcohols such as ethanol, ketones such as acetone and methylethylketone, preferably in the presence of a base such, for example, as $K_2CO_3$, KOH or NaOH. As a rule the reaction temperature is between 50°C and 100°C. The compounds of formula 13 are obtainable, for example, by reacting a compound of the formula 14 with a compound of the formula 15 whilst heating in the presence of a base. Subsequently the group $R_{11}$, a benzyl group or a methoxymethyl group, is split off by acid hydrolysis.

The compounds of the formula 1 in which R is a hydroxy group and $R_2$ is a hydroxymethyl group may also be obtained by ring closure of a compound of the formula 16 or a tautomer thereof, for example in a diluted aqueous solution of a base, at about 50°C to 100°C.

The compounds of the formula 16 are obtainable by condensing a compound of the formula 14 under alkaline conditions with an epihalogenhydrin, subsequent acid hydrolysis to split off the group $R_{11}$ and reaction with an aqueous solution of a base.

Compounds of the formula 1 in which R represents a hydroxy group and $R_1$ represents a carboxyl group are obtainable by hydrolysing a compound of the formula 17. The reaction is preferably carried out with a strong base in, for example, ethanol or with a strong acid in water at temperatures between room temperature and the boiling point of the mixture. The compounds of the formula 17 are obtainable by methods analogous to the above described methods.

When a compound of the formula 17 is hydrolysed under mild conditions, carboxylamides of the formula 1 in which R represents a hydroxy group are obtained. This reaction is usually carried out under acid conditions, for example in a mixture of glacial acetic acid and dilute hydrochloric acid, at room temperature or a slightly elevated temperature, for example between 40°C and 50°C.

The compounds of the formula 1 in which R represents a hydroxy group and R' represents an esterified carboxyl group may be prepared from compounds of the formula 17 by alcoholysis with the alcohol with which the carboxyl group is to be esterified. This reaction is carried out under acid conditions at temperatures up to the boiling point of the mixture. The intermediately formed imino esters are decomposed with water.

The compounds of the formula 1 in which R represents a hydroxy group may also be obtained by hydrolysing a compound of the formula 18 to substitute an oxygen atom for the halogen atom Hal.

The reaction is carried out in an inert solvent such, for example, as an alcohol to which a small amount of water has been added. If required the medium may be acidified. The temperature of the mixture is preferably raised to about 100°C to increase the reaction velocity.

The compounds of the formula 18 are obtained by reacting compounds of the formula 19 with more than 2 equivalents of a phosphorus oxyhalide.

The carboxylic acids of the formula 1 in which R represents a hydroxy group may alternatively be obtained in that in a compound of the formula 20 in which Hal is a halogen atom and $p = 3$, hydroxy is substituted for halogen and protected amino and hydroxy groups in $R'_2$ and $R'_3$ are converted into free hydroxy and amino groups. The reaction may be carried out in an alcoholic or aqueous solution of mixed alkali at temperatures between room temperature and the boiling point of the mixture.

In the same manner aldehydes of the formula 1 in which R represents a hydroxy group are obtainable from compounds of the formula 20 ($p = 2$).

Compounds of the formula 1 in which R represents a hydroxy group and $R_1$ represents a hydroxymethyl group are obtained by substituting hydroxy for halogen in a compound of the formula 20 ($p = 1$). The reaction may be carried out with silver hydroxide in an inert solvent such, for example, as dimethylformamide.

The compounds of the formula 20 are obtained by one of the aforementioned cyclization reactions.

Compounds of the formula 1 in which R represents an alkoxy group are obtainable by converting a compound of the formula 18 with an alcoholate. The reaction may be carried out in a solvent, preferably an alcohol which corresponds to the alcohol from which the alcoholate is derived. Preferably sodium alcoholates are used which are reacted at temperatures between 20°C and 80°C.

Compounds of the formula 1 in which R represents a mercapto or an alkylthio group are obtainable by reacting a compound of the formula 18 with an alkali hydrosulfide or an alkali mercaptide. The reaction is preferably carried out with a slight excess of reagent in an alcohol as a solvent at temperatures up to about 80°C.

Compounds of the formula 1 in which R represents a hydroxy group and $R_1$ represents a carboxylamide group are obtainable by reacting a compound of the formula 1 in which $R_1$ represents an alkoxycarbonyl group with ammonia. The reaction may be carried out by shaking the compound of the formula 1 with a concentrated aqueous solution of ammonia at temperatures up to about 120°C.

Compounds of the formula 1 in which $R_1$ represents an α-hydroxyalkyl group are obtainable by reducing a compound of the formula 1 in which $R_1$ represents an acyl group, a carboxyl group or an alkoxycarbonyl group with a hydride; the hydride may be a solution of lithium aluminium hydride or of sodium boron hydride in, for example, tetrahydrofuran or dioxan. The reaction temperature as a rule lies between 0°C and the boiling point of the solvent.

The compounds according to the invention may be brought into a form suitable for administration to the patient by known methods. The compounds may be worked up with solid and/or liquid excipients commonly used in pharmaceutics to form preparations such as powders, tablets, dragees, pills, suppositories, capsules, injection liquids and the like.

The invention will be set out more fully with reference to the following Examples.

EXAMPLES 1. 3-(ethoxymethyl)-2,3-dihydro-9-hydroxy-p-dioxino [2,3-g] quinoline-8-carboxylic acid ethylester.

a. 2-(ethoxymethyl)-7-nitro-1,4-benzodioxan obtained by ethylating 2-(hydroxymethyl)-7-nitro-1,4-benzodioxan (Gazz. Chim. Ital. 87, 1038-1049 (1957)) with diethylsulfate was hydrogenated by means of a palladium-on-carbon catalyst. The resulting amino was isolated as the hydrochloric acid salt. Melting point 130°C (1 aq.)

1.74 g of this substance was mixed with a solution of 1.45 g of 2-(ethoxymethylene)malonic acid diethylester in 20 ml of absolute ethanol. A solution of 0.71 g sodium acetate in 1.2 ml of water was added to the mixture, which ws then stored at room temperature for 8 hours. Subsequently the reaction mixture was concentrated in a vacuum and mixed with diethyl ether. The ethereal solution was washed with water and then with an aqueous sodium bicarbonate solution, dried over sodium sulfate and concentrated by evaporation. The residue was shaken with petroleum ether, whereupon 2- {[(2-ethoxymethyl)-1,4-benzodioxan-7-ylamino] methylene} malonic acid diethylester crystallized out. The substance was separated by filtration, washed with petroleum ether and dried in a vacuum. Melting point 68°-69°C.

b. 1.90 g of the obtained substance was dissolved in 25 ml of a mixture of 26.5 % by weight of diphenyl and 73.5% by weight of diphenylether and heated at 250°C for 40 minutes. After cooling the superscribed compound crystallized out. The substance was separated by filtration, washed with the mixture of diphenyl and diphenyl-ether, with ethanol and with diethylether. After recrystallization from ethanol the melting point was 266°C–268°C (with decomposition).

In analogous manners the following compounds were obtained, which all melt with decomposition:

2) 3-(methoxymethyl)-2,3-dihydro-9-hydroxy-dioxino [2,3-g] quinoline-8 carboxylic acid ethylester. Melting point 263°C–265°C.
3) 3-(ethoxymethyl)-2,3-dihydro-9-hydroxy-p-dioxino [2,3-g] quinolinyl-8-methylketone. Melting point 265°C–267°C.
4) 3-(ethocymethyl)-10-chloro-2,3-dihydro-9-hydroxy-p-dioxino [2,3-g] quinoline-8-carboxylic acid ethylester. Melting point 293°C–295°C.
5) 3-(n.propoxymethyl)-2,3-dihydro-9-hydroxy-p-dioxino [2,3-g] quinoline-8-carboxylic acid ethylester. Melting point 260°C–262°C.
6) 3-(n.butoxymethyl)-2,3-dihydro-9-hydroxy-p-dioxino [2,3-g] quinoline-8-carboxylic acid ethylester. Melting point 245°C–248°C.
7) 3-(isobutoxymethyl)-2,3-dihydro-9-hydroxy-p.dioxino [2,3-g] quinoline-8-carboxylic acid ethylester. Melting point 258°–262°C.
8) 3-(allyloxymethyl)-2,3-dihydro-9-hydroxy-p-dioxino [2,3-g] quinoline-8-carboxylic acid ethylester. Melting point 254°C–256°C.
9) 3-(cyclopentyloxymethyl)-2,3-dihydro-9-hydroxy-p-dioxino [2,3-g] quinoline-8-carboxylic acid ethylester. Melting point 257°C–260°C.
10) 3-(benzyloxymethyl)-2,3-dihydro-9-hydroxy-p-dioxino [2,3-g] quinoline-8-carboxylic acid ethylester. Melting point 236°C –238°C.
11) 3- [ (2-methoxyethoxy)methyl] -2,3-dihydro-9-hydroxy-p-dioxino -[2,3-g] quinoline-8-carboxylic acid ethylester. Melting point 228°C –231°C.
12) 3-(methylthiomethyl)-2,3-dihydro-9-hydroxy-p-dioxino [2,3-g] quinoline-8-carboxylic acid ethylester. Melting point 272°C –275°C.
13) 3-(ethoxymethyl)-2,3-dihydro-9-hydroxy-p-dioxino [2,3-g] quinoline-8-carboxylamide. Melting point 290°c – 292°C.
14) 3-(ethoxymethyl)-2,3-dihydro-9-hydroxy-p-dioxino [2,3-p] quinoline-8-carboxylic acid n.propylester.

a. A solution of 0.15 g of the acid corresponding to the abovementioned ester in 2 ml of thionylchloride was boiled for 20 minutes. The excess of thionylchloride was then distilled off in a vacuum. The substance obtained: 3-(ethoxymethyl)-9-chloro-2,3-dihydro-p-dioxino [2,3-g] quinoline-8-carboxylchloride was dissolved in 5 ml of n-propanol. The solution was heated at 70°C for 10 minutes.

b. A drop of water was added to the solution. The mixture was boiled for 90 minutes, concentrated in a vacuum and taken up in 4 ml of water. The resulting suspension was separated in a centrifuge, the liquid was poured off and the residue was crystallized from n.propanol. Melting point 270°C –271°C with decomposition.

15) 3-(ethoxymethyl)-2,3-dihydro-9-hydroxy-dioxino [2,3-g] quinoline-8-carboxylic acid ethylester.

6.27 ml of absolute ethanol was added drop by drop with vigorous stirring to a cooled mixture of 10.1 g of phosphorus pentoxide and 19.2 ml of anhydrous xylene in 10 minutes. The mixture was heated to 70°C and mixed with 11.4 g of { [(2-ethoxymethyl)-1,4-benzodioxan-7-ylamino-] methylene } malonic acid diethylester. The mixture was boiled for 30 minutes, then poured in about 50 ml of water and stirred for 1 hour. The solid substance formed was filtered off, stirred with a mixture of 25 ml of acetone and 25 ml of diethylether and filtered off again. The substance was crystallized from dimethylformamide, washed with diethylether and dried. Melting point 266°C–268°C with decomposition.

16) 3-(ethoxymethyl)-2,3-dihydro-9-hydroxy-p-dioxino [2,3-g] quinoline-8-carboxylic acid ethylester.

a. A solution of 3.0 g of { [(2-ethoxymethyl)-1,4-benzodioxan-7-ylamino] methylene } malonic acid diethylester in 30 ml of phosphorous oxychloride and 3 ml of triethylamine was boiled for well over 1 hour. The reaction mixture was then concentrated in a vacuum, the concentrate was dissolved in methylenechloride and the solution was shaken with water. Subsequently sodium carbonate was added until the mixture had become weakly alkaline, after which the layers were separated. The methylenechloride solution was washed with water, dried and concentrated. The concentrate was chromatographed on a column of silicagel (eluent methylenechloride). This resulted in 9-chloro-2,3-dihydro-3-(ethoxymethyl)-p-dioxino [2.3-g] quinoline-8-carboxylic acie ethylester having a melting point of 106°C–108°C.

b. A solution of 0.30 g of this chlorine compound in 4 ml of ethanol was mixed with 0.1 ml of concentrated hydrochloric acid, after which the mixture was boiled under a reflux condenser for 1½ hours. The reaction mixture was then concentrated by evaporation in a vacuum and the concentrate was mixed with 4 ml of water. The resulting precipitate was separated off and crystallized from ethanol. Melting point 266°C–268°C with decomposition.

The following compounds were obtained by analogous methods:

17) 3-(hydroxymethyl)-2,3-dihydro-9-hydroxy-p-dioxino [2,3-g] quinoline-8-carboxylic acid ethylester. Melting point 260°C.
18) 3-(ethoxymethyl)-2,3-dihydro-9-hydroxy-p-dioxino [2,3-g] quinoline-8-methanol. Melting point 278°C–279°C, partial decomposition below the melting point.
19)b 3-(ethoxymethyl)-2,3-dihydro-9-hydroxy-p-dioxino [2,3-g] quinoline-8-carboxylic acid.

a) 2-( [2-(ethoxymethyl)-1,4-benzodioxan-7-yl.amino]-2-cyanoacrylic acid ethyl ester (melting point 85°C–86°C) was obtained by reacting 7-amino-2-(ethoxymethyl)-1,4-benzodioxan (Example 1) with 2-cyano-2-ethoxy acrylic acid ethyl ester in boiling ethanol for 1 hour. The product was cyclized in the manner described in Example 1 to form 3-(ethoxymethyl)-2,3-dihydro-9-hydroxy-p-dioxino [2,3-g] quinoline-8-carbonitrile. Melting point 248°C–254°C with decomposition.

b. A suspension of 2.0 g of this carbonitrile in 50 ml of 1n-solution of caustic soda was boiled for 6 hours. After cooling, the reaction liquid was filtered and the filtrate was acidified with 4.5 ml of concentrated hydrochloric acid. The resulting precipitate was sucked off, washed with water and dried in a vacuum. Melting point 261°C–262°C with decomposition.

20) 3-(Ethoxymethyl)-2,3-dihydro-9-chloro-p-dioxino [2,3-g] quinoline-8-carboxylic acid ethylester a. A solution of 3.0 g of { [2-(ethoxymethyl)-1,4-benzodioxan-7-ylamino] methylene } malonic acid diethyl ester in 30 ml of phosphorus oxychloride and 3 ml of triethylamine was boiled under a reflux condenser for well over 1 hour. Subsequently the reaction mixture was concentrated in a vacuum and the concentrate was dissolved in methylenchloride and shaken with water. The mixture was mixed with sodium carbonate until it was weakly alkaline, after which the layers were separated. The methylene chloride solution was washed with water, dried and concentrated. The concentrate was chromatographed on a silicagel column (eluent methylene chloride). As a result 9-chloro-2,3-dihydro-3-(ethoxymethyl)-p-dioxino [2,3-g] quinoline-8-carboxylic acid ethylester was obtained, which has a melting point of 106°C–108°C.

3-(Ethoxymethyl)-2,3-dihydro-9-methoxy-p-dioxino [2,3-g] quinoline-8-carboxylic acid methylester.

b. The superscribed ester was obtained by reacting 1.2 g of the aforementioned compound in a boiling solution of 0.23 g of sodium in 6 ml of methanol for 5 minutes. The substance was isolated by concentrating the reaction mixture by evaporation in a vacuum, diluting the concentrate with water and extracting it with diethylether. The extract was dried, concentrated, chromatographed (silicagel and gradient elution with benzene/ acetone) and crystallized from ether-petroleum ether. Melting point 95°C–99°C.

21) 9,10-dichloro-3-(ethoxymethyl)-2,3-dihydro-p-dioxino [2,3-g] quinoline-8-carboxylic acid ethylester.

5 g of 10-chloro-3-(ethoxymethyl)-2,3-dihydro-9-hydroxy-p-dioxino [2,3-g] quinoline-8-carboxylic acid ethylester was mixed with 50 ml of phosphorus oxychloride and subsequently refluxed for 16 hours. The excess of phosphorus oxychloride was then distilled off in a vacuum, and the residue was mixed with water and methylene chloride. The separated solution in methylene chloride was washed thrice with portions of 25 of water and then dried over anhydrous sodium sulfate, after which the solvent was removed by distillation in a vacuum. The crystalline residue was chromatographed on a column comprising 50 g of silicagel, using a methylene chloride-acetone mixture as the eluent. Melting point 112°C–114°C.

22) 10-chloro-3-(ethoxymethyl)-2,3-dihydro-9-methoxy-p-dioxino [2,3-g] quinoline-8-carboxylic acid ethylester.

A mixture of 1 g of 9,10-dichloro-3-(ethoxymethyl)-2,3-dihydro-p-dioxino [2,3-b] quinoline-8-carboxylic acid ethylester and 0.2 g of sodium methylate in 10 ml of methanol was refluxed for 15 minutes. The reaction mixture was then concentrated in a vacuum and the concentrate was mixed with methylene chloride, hexane and water. The methylenchloridehexane solution was washed until neutral with water, dried and concentrated. The concentrate was crystallized from diethylether. Melting point 85°C–88°C.

23) 3-(ethoxymethyl)-2,3-dihydro-9-mercapto-p-dioxino [2,3-g] quinoline-8-carboxylic acid ethylester.

A solution of 1.78 g of 9-chloro-3-(ethoxymethyl)-2,3-dihydro-dioxino [2,3-g] quinoline-8-carboxylic acid ethylester, which had been prepared by a method analogous to that described in Example 20a, in 30 ml of ethanol and 1 ml of methylene chloride was slowly (in about 1 hour) added drop by drop, with stirring, to a solution of 0.74 g of sodium hydrogen sulfide in 20 ml of 70% ethanol. Stirring was continued for some time at room temperature, and subsequently the mixture was concentrated in a vacuum. The concentrate was mixed with methylenechloride and water; the layers were separated. The water layer was washed with methylene chloride. The solution in methylene chloride was washed with water, then twice with 2 N solution of caustic soda, and again with water. The alkaline washing liquid was acidified with concentrated hydrochloric acid and then extracted 3 times with methylene chloride. The collected extracts were washed with water and, after being dried and concentrated, chromatographed on a column comprising 25 g of silicagel with the use of methylene chloride with from 10 to 100% of acetone as the eluent (gradient elution). By crystallization of the chromatographed substance from isopropanol the superscribed substance was obtained. Melting point 199°C–202°C.

24a) 10-chloro-3-(ethoxymethyl)-2,3-dihydro-9-hydroxy-p-dioxino [2,3-g] quinoline-8-carboxylic acid.

4.0 g of the ethyl ester of the above-mentioned acid were dissolved in a mixture of 50 ml of ethanol and 50 ml of 2N solution of caustic soda. The solution was then refluxed for 1 hour, cooled, filtered and acidified with concentrated hydrochloric acid to pH 3. The precipitate produced was drawn off, washed respectively with 50 ml of ethanol, 100 ml of an ethanol/ether mixture 1 : 1 and 100 ml of ether, and dried. Melting point 226°C–267°C.

b. 10-chloro-3-(ethoxymethyl)-2,3-dihydro-9-p-dioxino [2,3-g] quinoline-8-carboxylic acid allyl ester.

A solution of 0.17 g of the carboxylic acid obtained by the method described in Example 24a in 2 ml of thionyl chloride was boiled with stirring for half an hour. The obtained suspension was then concentrated in a vacuum, mixed with 4 ml of anhydrous allyl alcohol and then heated to complete solution. After 1 hour 1 drop of water was added. The solution was heated at about 90°C for half an hour. Then the liquid was concentrated by evaporation in a vacuum, and the concentrate was mixed with water and diethyl ether. The resulting solid substance as sucked off and washed with diethyl ether and water to which 2ml of 1.5 N ammonia had been admixed, and again sucked off, washed with 1.5 N ammonia, water and diethyl ether and finally dried in a vacuum. After crystallization from dimethyl formamide the melting point was 263°C–265°C.

In a manner analogous to that described in Example 24b the following substances were obtained:

25) 10-chloro-3-(ethoxymethyl)-2,3-dihydro-9-hydroxy-p-dioxino [2,3-g] quinoline-8-carboxylic acid (2-ethoxyethyl) ester.

Melting point 248°C–250°C.

26) 10-chloro-3-(ethoxymethyl)-2,3-dihydro-9-hydroxy-p-dioxino [2,3-g] quinoline-8-carboxylic acid cyclopentyl ester.

Melting point 266°C–268°C.

27) 10-chloro-3-(ethoxymethyl)-2,3-dihydro-9-hydroxy-p-dioxino [2,3-g] quinoline-8-carboxylic acid (cyclopropylmethyl) ester.

Melting point 255°C-257°C.

28a) 9-chloro-3-(ethoxymethyl)-2,3-dihydro-10-nitro-p-dioxino [2,3-g] quinoline-8-carboxylic acid ethyl ester.

13.2 g of 9-chloro-3-(ethoxymethyl)-2,3-dihydro-p-dioxino [2,3-g] quinoline-8-carboxylic acid ethyl ester was added in batches, with stirring and cooling to from −15°C to −10°C, to 130 ml of fuming nitric acid. Stirring at a temperature between −15°C and −10°C was continued for half an hour. Then the reaction mixture was poured into 1,500 ml of water, and this mixture was extracted four times with methylene chloride. The extracts were washed with water until neutral, dired and concentrated. The concentrate was chromatographed on a column comprising 200 g of silicagel with the use of the methylene chloride containing up to 12% of acetone as the eluent (gradient elution). Melting point 139.5°C–140.5°C.

b) 3-(ethoxymethyl)-2,3-dihydro-9-hydroxy-10-nitro-p-dioxino [2,3-g] quinoline-8-carboxylic acid ethyl ester.

3.5 g of the substance obtained by the method described in Example 28a) was mixed with 35 ml of acetic acid and 7.0 g of sodium acetate. The mixture was refluxed for 4 hours. After it had been cooled it was mixed with water; the solid substance produced was sucked off, washed thrice with water, then once with ethanol and finally dried. Melting point about 300°C with decomposition.

29) 10-amino-3-(ethoxymethyl)2,3-dihydro-9-hydroxy-p-dioxino [2,3-g] quinoline-8-carboxylic acid ethyl ester.

A suspension of 3.77 g of 3-(ethoxymethyl)-2,3-dihydro-9-hydroxy-10-nitro-p-dioxino [2,3-g] quinoline-8-carboxylic acid ethyl ester, obtained by the method described in Example 28b), in 300 ml of ethanol was added to a prehydrogenated suspension of 0.3 g of platinum oxide (Adams catalyst) in ethanol. The suspension was hydrogenated at room temperature under a pressure of about 1.1 atmosphere until the nitro group had been reduced to an amino group. The reaction mixture was then heated and filtered while hot. The filtrate was concentrated by evaporation in a vacuum, and the solid residue was crystallized from absolute ethanol. Melting point 253°C– 256°C with decomposition.

30a) 2- { [2-(ethoxymethyl)-5-(trifluoromethyl-1,4-benzodioxan-7-ylamino] -methylene } malonic acid diethyl ester.

2-benzyloxy-4-nitrophenyl was iodinated to 2-benzyloxy-6-iodo-4-nitrophenol of melting point 143°C–145°C in the manner described for an analogous compound in J.Am.Chem. Soc. 75 4290 (1953). This compound was converted with epichlorohydrine into 2-(hydroxymethyl)-5-iodo-7-nitro-1,4-benzodioxane by the method described in J.Ned. Chem. 1965 page 455 for an analogous compound. The substance obtained was ethylated to 2-(ethoxymethyl)-5-iodo-7-nitro-1,4-benzodioxane (melting point of the crude product 90°–-99°C), and this was converted with CF₃J and powdered copper in dimethylformamide into 2-(ethoxymethyl)-7-nitro-5-(trifluoromethyl)-1,4-benzodioxan by the method described in Tetrahedron Letters 1969 pages 4095–4096. The reaction product was hydrogenated by means of a palladium on active carbon catalyst at room temperature and under a pressure of about 1.1 atmospheres to form 7-amino-2-(ethoxymethyl)-5-(trifluoromethyl)-1,4-benzodioxan, which was immediately converted with 2-(ethoxymethylene)-malonic acid diethyl ester into 2- { [2-(ethoxymethyl)-5-(trifluromethyl)-1,4-benzodioxan-7-ylamino] -methylene } malonic acid diethyl ester which had a melting point of 96°–98°C.

b) 3-(ethoxymethyl)-2,3-dihydro-9-hydroxy-10-(trifluoromethyl)-p-dioxino [2,3-g] quinoline-8-carboxylic acid ethyl ester.

1.2 g of the compound obtained by the method described in Example 30a) was dissolved in 12 ml of a mixture of 26.5 per cent by weight of diphenyl and 73.5 per cent by weight of diphenyl ether. The solution was mixed with 0.12 ml of quinoline and subsequently maintained at a temperature between 245°C and 250°C whilst stirring in a nitrogen atmosphere for 20 minutes. After the reaction mixture had cooled, it was diluted with 12 ml of petroleum ether, the crude product crystallizing out. It was sucked off, washed with petroleum ether and subsequently, by selective crystallization from dimethylformamide, separated from the simultaneously formed by-product 3-(ethoxymethyl)-2,3-dihydro-5-hydroxy-10-(trifluoromethyl)-p-dioxino [2,3-f] quinoline-6-carboxylic acid ethyl ester. The superscribed compound had a decomposition point at about 250°C.

3-(ethoxymethyl)-2,3-dihydro-8-(1-hydroxoethyl)-9-hydroxy-p-dioxino [2,3-g] quinoline.

A suspension of 0.58 g of 3-(ethoxymethyl)-2,3-dihydro-9-hydroxy-p-dioxino [2,3-g] quinolinyl-8-methyl ketone in 50 ml of methanol was mixed with 0.12 g of sodium boron hydride and the mixture was stirred at room temperature for 1.5 hours. Subsequently a further amount of 0.05 g of sodium boron hydride was added, the mixture was stirred for 16 hours, a still further amount of 0.1 g of sodium boron hydride was added, after which stirring was continued at 50°C for 0.5 hour. The obtained solution was mixed with 5 ml of water and the mixture was concentrated by evaporation in a vacuum. The residual mass was mixed with 30 ml of water and 30 ml of chloroform, whereupon 3-

(ethoxymethyl)-2,3-dihydro-8-(1-hydroxyethyl)-9-hydroxy-p-dioxino [2,3-g] quinoline crystallized out. This was drawn off and washed successively with water, a 1 : 1 (v/v) acetone-ether mixture and ether. The substance melts at 177°C – 179°C with decomposition.

32) 10-(acetylamino)-3-(ethoxymethyl)-2,3-dihydro-9-hydroxy-p-dioxino [2,3-g] quinoline-8-carboxylic acid ethyl ester 3 portions of acetic acid anhydride totalling 3 ml were added at intervals of half an hour to a suspension of 0.13 g of 10-amino-3-(ethoxymethyl)-2,3-dihydro-9-hydroxy-p-dioxino [2,3-g] quinoline-8-carboxylic acid ethyl ester obtained by the method described in Example 29) in 15 ml of 96% ethanol. Before the last addition the reaction mixture was briefly heated to about 50°C, a clear solution being obtained. After the last addition the mixture was stirred for another hour and subsequently concentrated by evaporation in a vacuum. The concentrate was mixed with methylene chloride and water, after which the two layers were separated. The water layer was extracted 2 times with methylene chloride, the entire solution in methylene chloride was then washed thrice with water and subsequently dried over anhydrous sodium sulfate. Subsequently the solvent was distilled off in a vacuum. The residue having the superscribed structure was not purified any further.

33) 3-(ethoxymethyl)-8-ethyl-2,3-dihydro-9-hydroxy-p-dioxino [2,3-g] -g]

A mixture of 0.90 g of 3-(ethoxymethyl)-2,3-dihydro-9-hydroxy-dioxino [2,3-g] quinolyl-8-methyl ketone, 10 ml of triethylene glycol, 0.50 ml of hydrazine hydrate and 0.40 g of potassium hydroxide was heated at 100°C for half an hour, the ketone dissolving. The reaction mixture was slowly heated to 115°C in a flask provided with a short fractionating column, held at this temperature for one hour and then held at a temperature between 175°C and 185°C for 5 hours. After the mixture had cooled, it was mixed with 0.50 ml of glacial acetic acid. The potassium acetate which as a result crystallized was removed by filtering. The filtrate was concentrated to about 3 g in a vacuum at a temperature of about 160°C. The concentrate was chromatographed on a column comprising 100 g of silicagel with the use of a 1 : 1 (v/v) methylene chloride/acetone mixture as the eluent. The fraction having a Rf value of 0.29 (on a silicagel plate using the same eluent) was crystallized from a mixture of acetone and diethyl ether. Melting point 166°C–168°C.

34) 3-(ethoxymethyl)-2,3-dihydro-9-hydroxy-p-dioxino [2,3-g] quinoline-8-methanol.

0.30 g of 3-(ethoxymethyl)-2,3-dihydro-9-hydroxy-p-dioxino [2,3-g] quinone-8-carboxylic acid ethyl wster was added to a suspension of 0.08 g of lithium aluminium hydride in 30 ml of anhydrous tetrahydrofuran. The mixture was refluxed for one hour. Then 0.5 ml of water was added drop by drop, after which the mixture was boiled for a few minutes more. The resulting precipitate was drawn off, washed with tetrahydrofuran and extracted with 40 ml of absolute ethanol. From the first filtrate and from the ethanol extract the solvents were removed by distillation in a vacuum. The residue was mixed with 5 ml of water. The solution obtained was filtered. 1.8 ml of 1 N acetic acid solution was added to the filtrate, with the result that the superscribed compound crystallized out. The substance was drawn off, washed with water and dried in a vacuum. Melting point 268°C –279°C (decomposes partly below the melting point).

35) 3-(hydroxymethyl)-2,3-dihydro-9-hydroxy-p-dioxino [2,3-g] quinoline-8-carboxylic acid ethyl ester.

A warm solution of 0.20 g of 3-(benzyloxymethyl)-2,3-dihydro-9-hydroxy-p-dioxine [2,3-g] quinoline-8-carboxylic acid ethyl ester in 50 ml of ethanol and 0.20 ml of 4,4 N hydrochloric acid was added to a prehydrated suspension of 0.03 g of platinum oxide (according to Adams) in ethanol. The mixture was hydrogenated at room temperature at a pressure of about 1.1 atmosphere until the benzyl group had been split off. The catalyst was then removed by filtration. The filtrate was concentrated in a vacuum to about 10 g. Subsequently 0.54 ml of 1.62 N ammonia was added, after which the solution was further concentrated. By diluting the concentrate with diethyl ether the superscribed hydroxymethyl compound precepitated. The substance was drawn off, washed with diethylether and dried. Melting point 260° with decomposition.

36) 3-(ethoxymethyl)-2,3-dihydro-9-hydroxy-p-dioxino [2,3-g] quinoline-8-carboxylic acid.

A suspension of 2.86 g of 3-(ethoxymethyl)-2,3-dihydro-9-hydroxy-p-dioxino [2,3-] quinoline-8-carboxylic acid ethyl ester in 50 ml of 1 n sodium hydroxide was boiled for one hour and then, still hot, acidified with 4.5 ml of concentrated hydrochloric acid. As a result the superscribed compound precipitated in the form of crystals. The substance was drawn off, washed with portions of water totalling about 50 ml and dried in a vacuum. Melting point 261°C–262°C with decomposition.

37) 3-(ethoxymethyl)-2,3-dihydro-9-hydroxy-p-dioxino [2,3-g] quinoline-8-carboxamide.

A suspension of 0.30 g of 3-(ethoxymethyl)-2,3-dihydro-9-hydroxy-p-dioxino [2,3-g] quinoline-8-carboxylic acid ethyl ester in 10 ml of concentrated ammonia was shaken in closed tube at 90°C for 9 hours. The resulting solution was cooled, the tube was opened, the solution was filtered and the filtrate was concentrated by evaporation in a vacuum to about 5 g. The resulting precipitate was drawn off and then crystallized from 6 ml of 80% ethanol. Melting point 290°C – 299°C (with decomposition).

38) 10-chloro-3-(ethoxymethyl)-2,3-dihydro-9-hydroxy-p-dioxino [2,3-g] quinoline-8-carboxylic acid ethyl ester.

A solution of 5 g of 2- { [5-chloro-2-(ethoxymethyl)1,4-benzodioxan-7-ylamino ] methylene} malonic acid diethyl ester obtained by a method analous to that described in Example 1a) in 50 ml of a mixture comprising 26.5 per cent by weight of diphenyl and 73.5 per cent by weight of diphenyl ether was mixed with 0.5 ml of quinoline and then heated with stirring in a nitrogen atmosphere to 245°C in 15 minutes. The mixture was stirred in a nitrogen atmosphere at a temperature between 245°C and 250°C for 45 minutes and then slowly cooled to room temperature. The crystallized substance was drawn off, washed with 75 ml of a 1 : 3 ethanol/diethyl ether mixture, dried and crystallized from dimethyl formamide. Melting point 293°–295°C with decomposition.

39) 10-chloro-3-(ethoxymethyl)-2,3-dihydro-9-hydroxy-p-dioxino [2,3-g] quinoline-8-carboxylic acid ethyl ester.

A mixture of 1 g of 2- { [5-chloro-2-(ethoxymethyl)-1,4-benzodioxan-7-ylamino] methylene } malonic acid diethyl ester and 10 ml of paraffin oil was heated at 240°C for 25 minutes. When the mixture had slowly been cooled and no substance crystallized anymore, 10 ml of acetone and 5 ml of diethyl ether were added. The solid reaction product was drawn off and washed with diethyl ether. It was crystallized from dimethyl formamide. Melting point 293°C–295°C with decomposition.

40) 3-(ethoxymethyl)-2,3-dihydro-9-hydroxy-p-dioxino- [2,3-g] quinoline-8-carboxylic acid ethyl ester.

A mixture of 0.4 g of 2- { [2-(ethoxymethyl)-1,4-benzodioxan-7-ylamino] methylene } malonic acid diethyl ester obtained by the method described in Example 1a) and 2 g of polyphosphoric acid ethyl ester (J. Chem. Soc. 1972 173) was heated at 120°C whilst stirring for 1.5 hours. After the reaction mixture had been cooled, it was mixed with 20 ml of water and then neutralized with sodium bicarbonate. The precipitate formed was drawn off and washed with water, with ethanol and with diethyl ether. The substance was further purified by several crystallizations from dimethylformamide. Melting point 266°C–268°C with decomposition.

41) 3-(ethoxymethyl)-2,3-dihydro-9-hydroxy-dioxino [2,3-g] quinoline-8-carboxylic acid ethyl ester.

a. 6.95 g of 7-amino-2-(ethoxymethyl)-1,4-benzodioxan obtained by the method described in Example 1a) was dissolved in 35 ml of water and 2.83 ml of concentrated hydrochloric acid, and the mixture was added to a solution of 5.95 chloralhydrate in 85 ml of water, the resulting solution being mixed with a solution of 86.5 g of sodium sulfate in 335 ml of water and 7.32 g of hydroxylamine hydrochloride dissolved in 35 ml of water. The mixture was heated to boiling temperature in 50 minutes. It was then boiled under a reflux condenser for 5 minutes. After the mixture had been cooled, it was extracted with methylene chloride. The extract was washed with water, dried over anhydrous sodium sulfate and concentrated in a vacuum. The addition of petroleum ether caused 2-ethoxymethyl)-7-(2-isonitrosoacetamido)-1,4-benzodioxan to crystallize out. Melting point 103°C–106°C.

b. 3.64 g of the compound obtained by the method described in Example 41a) was added in batches whilst stirring to 10 ml of concentrated sulfuric acid heated to 50°C. The mixture was heated to 80°C and stirred at this temperature for 10 minutes. After the mixture had cooled it was poured into 120 ml of ice water, whereupon 3-(ethoxymethyl)-p-dioxino [2,3-f] isatin crystallized out. The substance was drawn off, washed free from acid with water and dried. Melting point 151°–153°C.

c. 0.13 g of the substance obtained by the method described in Example 41b) was dissolved in 0.9 ml of 2 N sodium hydroxide. 0.15 ml of 30% hydrogen peroxide solution was added with stirring. After the mixture had been stirred for some minutes, it was acidified with 2 N hydrochloric acid and then filtered. The filtrate was evaporated to dryness in a vacuum, and the residue was extracted thrice with absolute ethanol. The ethanolic extracts were concentrated by evaporation in a vacuum, dissolved in absolute ethanol and again concentrated. The concentration was stirred with petroleum ether, with the result that 7-amino-2-(ethoxymethyl)-1,4-benzodioxan-6-carboxylic acid crystallized out. Melting point 124°C–130°C with decomposition. Boiling unter a reflux condenser with methanolic hydrochloric acid for 1 hour gave the corresponding methyl ester.

d. A fresh solution of 5 g of the sodium salt of formyl acetic acid ethyl ester in 20 ml of water was added dropwise with stirring in about 10 minutes to a solution of 3.2 g of the ester obtained by the method described in Example 41c) in 20 ml of water. After the mixture had been stirred for 15 minutes, it was extracted with diethyl ether. The ethereal extract was dried, concentrated and chromatographed on a silicagel column. 1.00 g of the resulting 7- [2-(ethoxycarboxyl)-vinylamino] -2- (ethoxymethyl)-1,4-benzodioxan-6-carboxylic acid methyl ester was dissolved in 25 ml of absolute diethyl ether. A solution of 70 mg of sodium in 2 ml absolute ethanol was added dropwise in 2 minutes whilst stirring in a nitrogen atmosphere. After the mixture had been stirred for another 5 minutes, the produced 3-(ethoxymethyl)-2,3-dihydro-9-hydroxy-p-dioxino [2,3-g] quinoline-8-carboxylic acid ethyl ester was isolated by concentration and crystallization from dimethyl formamide. Melting point 266°C–268°C with decomposition.

42) 3-(hydroxymethyl)-2,3-dihydro-9-hydroxy-p-dioxino [2,3-g] quinoline-8-carboxylic acid.

a. 4-amino-2-benzyloxyphenol having a melting point of 106°C–108°C was obtained from the corresponding nitro compound by reduction with powdered iron and hydrochloric acid according to the method described in Houben-Weyl 11/1 page 399.

b. This substance was condensed with 2-(ethoxymethylene) malonic acid diethyl ester in the manner described in Example 1) to form 2- { [3-benzyloxy-4-hydroxyanilino] methylene } malonic acid diethyl ester in the form of an oil.

c. 1.74 g of the substance obtained by the method described in Example 42b) was diluted with 17 ml of a mixture of 26.5 per cent by weight of diphenyl and 73.5 per cent by weight of diphenyl ether. The solution was heated to 250°C and held at a temperature between 245°C and 250°C for 5 minutes. Subsequently the solution was slowly cooled, 7-benzyloxy-4,6-dihydroxyquinoline-3-carboxylic acid ethyl ester crystallizing out. The substance was drawn off, washed once with ethanol, thrice with diethyl ether and dried. Melting point 272°C–274°C.

d. 3.39 g of the compound obtained by the method described in Example 42c) was mixed with 3 ml of epichlorohydrin and 4 drops of piperidine. The mixture was heated to 100°C in a nitrogen atmosphere whilst stirring. Subsequently 7 ml of epichlorohydrin were added, after which the mixture was heated at 100°C with stirring for 2.5 hours. The reaction mixture was concentrated in a vacuum, a dark viscous oil being obtained which mainly consisted of 7-benzyloxy-6-(3-chloro-2-hydroxypropoxy)-4-hydroxyquinoline-3-carboxylic acid ethyl ester.

e. The product obtained by the method described in Example 42d) was dissolved in 27 ml of acetic acid. This solution was mixed with 19 ml of concentrated hydrochloric acid. This mixture was stirred at 100°C in a nitrogen atmosphere for one hour and then concentrated in a vacuum. The concentrate, a dark viscous oil, mainly consisted of 6-(3-chloro-2-hydroxy-propoxyl)-4,7-dihydroxyquinoline-3-carboxylic acid ethyl ester.

f. The concentrate of obtained by the method described in Example 42e) was mixed with 10 ml of 2N solution of caustic soda and an amount of water such as to enable the mixture to be thoroughly stirred. After stirring at room temperature for half an hour another portion of 10 ml of 2N solution of caustic soda was added, and the mixture was heated at 100°C with stirring in a nitrogen atmosphere for 2 hours, whilst after about one hour a further portion of 10 ml of 2N solution of caustic soda was added. After the reaction mixture had been cooled and filtered, it was acidified with concentrated hydrochloric acid, 2,3-dihydro-9-hydroxy-3-(hydroxymethyl)-p-dioxino [2,3-g] quinoline-8-carboxylic acid being precipitated. The substance was separated off, washed with water, ethanol and diethyl ether and dried. Melting point 230°–235°C with decomposition.

43) 3-(ethoxymethyl)-2,3-dihydro-9-hydroxy-10-chloro-p-dioxino [2,3-g] quinoline-8-carboxylic acid having a melting point of 266°C–267°C was obtained by the method described in Example 36) from the compound produced by the method described in Example 38).

The following compounds were obtained by methods analogous to that described in Example 1):

44) 3-(ethoxymethyl)-2,3-dihydro-9-hydroxy-p-dioxino [2,3-g] quinoline-8-carboxylic acid ethyl ester. Melting point 250°C–253°C.
45) 3-(acetoxymethyl)-2,3-dihydro-9-hydroxy-p-dioxino [2,3-g] quinoline-8-carboxylic acid ethyl ester. Melting point 271°C–274°C.
46) 3-(ethoxymethyl)-2,3-dihydro-9-hydroxy-10-methyl-p-dioxino [2,3-g] quinoline-8-carboxylic acie ethyl ester. Melting point 269°C–273°C.
47) 3-(ethoxymethyl)-2,3-dihydro-9-hydroxy-10-methoxy-p-dioxino [2,3-g] quinoline-8-carboxylic acid ethyl ester. This compound decomposes above 250°C.

By methods analogous to that described in Example 14) the following compounds were obtained:

48) 3-(ethoxymethyl)-2,3-dihydro-9-hydroxy-dioxino [2,3-g] quinoline-8-carboxylic acid methyl ester. Melting point 257°C–260°C.
49) 3-(ethoxymethyl)-2,3-dihydro-9-hydroxy-p-dioxino [2,3-g] quinoline-8-carboxylic acid isobutyl ester. Melting point 166°C–167°C.

a. Tablet containing 0.05 g of 3-(ethoxymethyl)-9-hydroxy-10-nitro-2,3-dihydro-p-dioxino [2,3-g] quinoline-8-carboxylic acid ethyl ester.

100 g of 3-(ethoxymethyl)-9-hydroxy-10-nitro-2,3-dihydro-p-dioxino [2,3-g] quinoline-8-carboxylic acid ethyl ester was mixed with 190 g of secondary calcium phosphate, 90 g of microcrystalline cellulose and 120 g of a mixture consisting of 20 parts by weight of maize starch, 32 parts by weight of talc and 4 parts by weight of magnesium stearate, until a homogeneous mixture had been obtained. From this mixture tablets were struck which each had a diameter of 7.5 mm and a weight of 250 mg.

b. Suppository containing 0.05 g of 3-(ethoxymethyl)-9-hydroxy-10-nitro-2,3-dihydro-p-dioxino [2,3-g] quinoline-8-carboxylic acid n.propyl ester.

50 mg of 3-(ethoxymethyl)-9-hydroxy-10-nitro-2,3-dihydro-p-dioxino [2,3-g] quinoline-8-carboxylic acid n-propyl ester was mixed with 3 g of a suppository mass and shaped into the form of a suppository.

c. Injection liquid containing the sodium salt of 3-(ethoxymethyl)-2,3-dihydro-9-hydroxy-p-dioxino [2,3-g] quinoline-8-carboxylic acid.

10 g of 3-(ethoxymethyl)-2,3-dihydro-9-hydroxy-p-dioxino [2,3-g] quinoline-8-carboxylic acid were dissolved in an equimolar mount of diluted potassium hydroxide. The solution was mixed with a solution of 3 g of phenyl and the mixture was diluted with distilled water to a volume of 1,000 ml and filtered through a bacterial filter, after which ampoules of 1 or 2 ml each were aseptically filled with the diluted mixture.

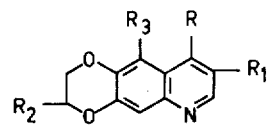

1

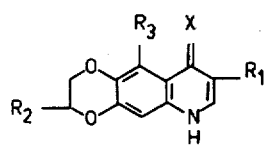

1a

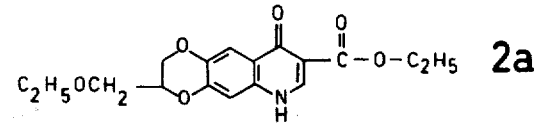

2a

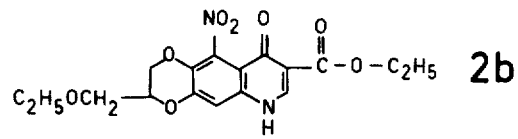

2b

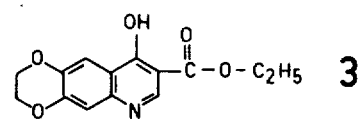

3

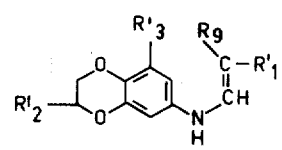

4

19
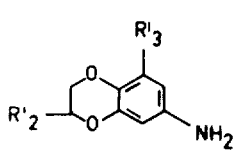
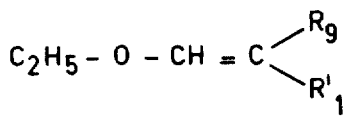
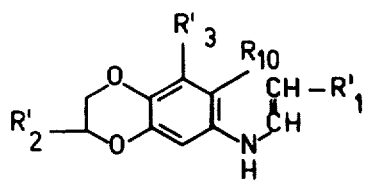
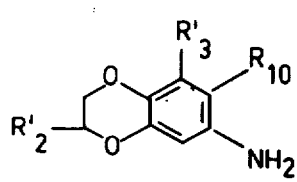
$C_2H_5 - O - CH = CH - R'_1$
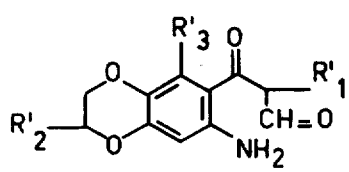
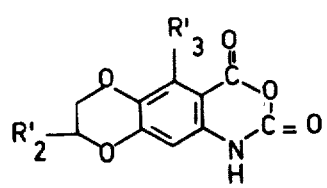
$O = CH - CH_2 - R'_2$
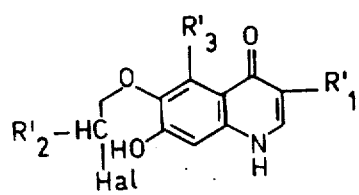
20
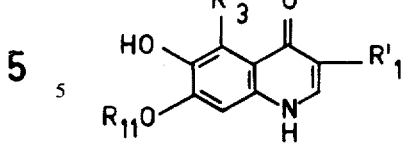 14
$R'_2 - CHHal - CH_2Hal$ 15
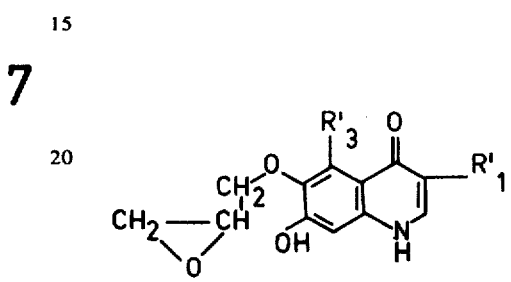 16
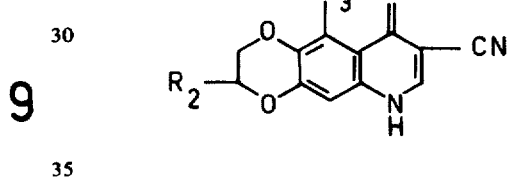 17
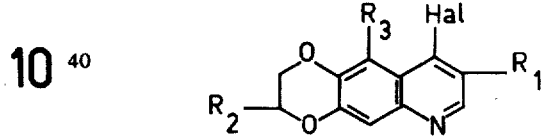 18
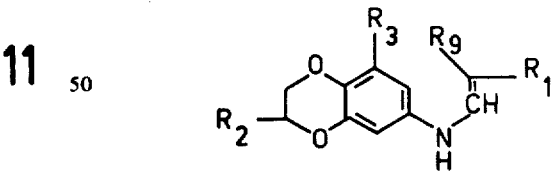 19
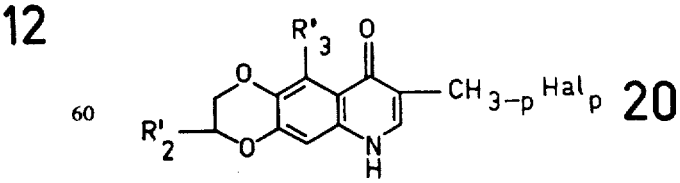 20
5
6
7
8
9
10
11
12
13
What is claimed is:
1. A diuretic composition comprising a diuretically effective dosage of a compound selected from the group consisting of quinolines of the formula

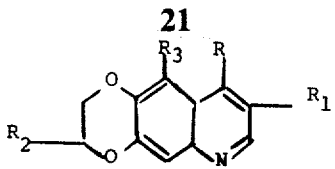

wherein R is hydroxy, $R_3$ is a substituent selected from the group consisting of hydrogen, halogen, trifluromethyl and nitro, $R_1$ is a substituent selected from the group consisting of alkoxycarbonyl, alkoxyalkoxycarbonyl, and carboxyl and $R_2$ is a substituent selected from the group consisting of alkoxyalkyl, alkoxyalkoxyalkyl, alkenylalkoxy, cycloalkylalkoxy and cycloalkenylalkoxy each of up to 6 carbon atoms and hydroxy alkyl of up to 4 carbon atoms, alkali metal salts thereof, tautomers thereof and acid addition salts thereof formed with pharmaceutically acceptable acids with the proviso that the number of carbons in the substituents defined by $R_1$ is at most four when $R_3$ is a substituent other than halogen or trifluoromethyl and is six when $R_3$ is halogen or trifluromethyl and a pharmaceutically acceptable carrier therefor.

2. The diuretic composition of claim 1 wherein $R_3$ represents a halogen atom.

3. The diuretic composition of claim 1 wherein the compound is a member selected from the group consisting of 3-(ethoxymethyl)-2,3-dihydro-9-hydroxy-p-dioxino [2,3-g] quinoline-8-carboxylic acid ethyl ester and salts thereof formed with pharmaceutically acceptable acids.

4. The diuretic composition of claim 1 wherein the compound is a member selected from the group consisting of 3-(methoxymethyl)-2,3-dihydro-9-hydroxy-p-dioxino [2,3-g]] quinoline-8-carboxylic acid ethyl ester and salts thereof formed with pharmaceutically acceptable acids.

5. The diuretic composition of claim 1 wherein the compound is a member selected from the group consisting of 3-(ethoxymethyl)-10-chloro-2,3-dihydro-9-hydroxy-p-dioxino[2,3-g]] quinoline-8-carboxylic acid ethyl ester and salts therefore formed with pharmaceutically acceptable acids.

6. The diuretic composition of claim 1 wherein the compound is a member selected from the group consisting of 3-(n-propoxymethyl)-2,3-dihydro-9-hydroxy-p-dioxino [2,3-g]] quinoline-8-carboxylic acid ethyl ester and salts thereof formed with pharmaceutically acceptable acids.

7. The diuretic composition of claim 1 wherein the compound is a member selected from the group consisting of 3-(n.butoxymethyl)-2,3-dihydro-9-hydroxy-p-dioxino [2,3-g] quinoline-8-carboxylic acid ethyl ester and salts thereof formed with pharmaceutically acceptable acids.

8. The diuretic composition of claim 1 wherein the compound is a member selected from the group consisting of 3-(isobutoxymethyl)-2,3-dihydro-9-hydroxy-p-dioxino [2,3-g] quinoline-8-carboxylic acid ethyl ester and salts thereof formed with pharmaceutically acceptable acids.

9. The diuretic composition of claim 1 wherein the compound is a member selected from the group consisting of 3-(allyloxymethyl)-2,3-dihydro-9-hydroxy-p-dioxino [2,3-g] quinoline-8-carboxylic acid ethyl ester and salts thereof formed with pharmaceutically acceptable acids.

10. The diuretic composition of claim 1 wherein the compound is a member selected from the group consisting of 3-(cyclopentyloxymethyl)-2,3-dihydro-9-hydroxy-p-dioxino [2,3-g] quinoline-8-carboxylic acid ethyl ester and salts thereof formed with pharmaceutically acceptable acids.

11. The diuretic composition of claim 1 wherein the compound is a member selected from the group consisting of 3-(benzyloxymethyl)-2,3-dihydro-9-hydroxy-p-dioxino [2,3-g] quinoline-8-carboxylic acid ethyl ester and salts thereof with pharmaceutically acceptable acids.

12. The diuretic composition of claim 1 wherein the compound is a member selected from the group consisting of 3-[(2-methoxyethoxy)-methyl]-2,3-dihydro-9-hydroxy-p-dioxino[2,3-g] quinoline -8-carboxylic acid ethyl ester and salts thereof with pharmaceutically acceptable acids.

13. The diuretic composition of claim 1 wherein the compound is a member selected from the group consisting of 3-(methylthiomethyl)-2,3-dihydro-9-hydroxy-p-dioxino [2,3-g] quinoline-8-carboxylic acid ethyl ester and salts thereof with pharmaceutically acceptable acids.

14. The diuretic composition of claim 1 wherein the compound is a member selected from the group consisting of 3-(ethoxymethyl)-2,3-dihydro-9-hydroxy p-dioxino [2,3-g] quinoline-8-carboxylic acid, alkali metal salts and salts thereof with pharmaceutically acceptable acids.

15. The diuretic composition of claim 1 wherein the compound is a member selected from the group consisting of 3-(hydroxymethyl)-2,3-dihydro-9-hydroxy-p-dioxino [2,3-g] quinoline-8-carboxylic acid ethyl ester and salts thereof with pharmaceutically acceptable acids.

16. The diuretic composition of claim 1 wherein the compound is a member selected from the group consisting of 3-(ethoxymethyl) -2,3-dihydro-9-hydroxy-p-dioxino [2,3-g] quinoline-8-carboxylic acid n.propyl ester and salts thereof with pharmaceutically acceptable acids.

17. The diuretic composition of claim 1 wherein the compound is a member selected from the group consisting of 3-(ethoxymethyl) -2,3-dihydro-9-methoxy-p-dioxino [2,3-g] quinoline-8-carboxylic acid methyl ester and salts thereof with pharmaceutically acceptable acids.

18. The diuretic composition of claim 1 wherein the compound is a member selected from the group consisting of 9,10-dichloro-3-(ethoxymethyl)-2,3-dihydro-p-dioxino [2,3-g] quinoline-8-carboxylic acid ethyl ester and salts thereof with pharmaceutically acceptable acids.

19. The diuretic composition of claim 1 wherein the compound is a member selected from the group consisting of 10-chloro-3-(ethoxymethyl)-2,3-dihydro-9-methoxy-p-dioxino [2,3-g] quinoline -8-carboxylic acid ethyl ester and salts thereof with pharmaceutically acceptable acids.

20. The diuretic composition of claim 1 wherein the compound is a member selected from the group consisting of 3-(ethoxymethyl) -2,3-dihydro-9-mercapto-p-dioxino [2,3-g] quinoline-8-carboxylic acid ethyl ester and salts thereof with pharmaceutically acceptable acids.

21. The diuretic composition of claim 1 wherein the compound is a member selected from the group consisting of 10-chloro-3-(ethoxymethyl)-2,3-dihydro-9-hydroxy-p-dioxino [2,3-g] quinoline-8-carboxylic acid allyl ester and salts thereof with pharmaceutically ac- 22. The diuretic composition of claim 1 wherein the compound is a member selected from the group consisting of 10-chloro-3-(ethoxymethyl)-2,3-dihydro-9-hydroxy-p-dioxino [2,3-g] quinoline-8-carboxylic acid (2-ethoxymethyl)ester and salts thereof with pharmaceutically acceptable acids.

23. The diuretic composition of claim 1 wherein the compound is a member selected from the group consisting of 10-chloro-3-(ethoxymethyl)-2,3-dihydro-9-hydroxy-p-dioxino [2,3-g] quinoline-8-carboxylic acid cyclopentyl ester and salts thereof with pharmaceutically acceptable acids.

24. The diuretic composition of claim 1 wherein the compound is a member selected from the group consisting of 10-chloro-3-(ethoxymethyl)-2,3-dihydro-9-hydroxy-p-dioxino [2,3-g] quinoline-8-carboxylic acid (cyclopropylmethyl) ester and salts thereof with pharmaceutically acceptable acids.

25. The diuretic composition of claim 1 wherein the compound is a member selected from the group consisting of 3-(ethoxymethyl)-2,3-dihydro-9-hydroxy-10-nitro-p-dioxino [2,3-g] quinoline-8-carboxylic acid ethyl ester and salts thereof with pharmaceutically acceptable acids.

26. The diuretic composition of claim 1 wherein the compound is a member selected from the group consisting of 10-amino-3-(ethoxymethyl)-2,3-dihydro-9-hydroxy-p-dioxino [2,3-g] quinoline-8-carboxylic acid ethyl ester and salts thereof with pharmaceutically acceptable acids.

27. The diuretic composition of claim 1 wherein the compound is a member selected from the group consisting of 3-(ethoxymethyl)-2,3-dihydro-9-hydroxy-10-(tri-fluoromethyl)-p-dioxino [2,3-g] quinoline-8-carboxylic acid ethyl ester and salts thereof with pharmaceutically acceptable acids.

28. The diuretic composition of claim 1 wherein the compound is a member selected from the group consisting of 3-(hydroxymethyl)-2,3-dihydro-9-hydroxy-p-dioxino [2,3-g] quinoline-8-carboxylic acid, alkali metal salts and salts thereof with pharmaceutically acceptable acids.

29. The diuretic composition of claim 1 wherein the compound is a member selected from the group consisting of 3-(ethoxymethyl)-2,3-dihydro-9-hydroxy-10-chloro-p-dioxino [2,3-g] quinoline-8-carboxylic acid, alkali metal salts and salts thereof with pharmaceutically acceptable acids.

30. The diuretic composition of claim 1 wherein the compound is a member selected from the group consisting of 3-(ethoxymethyl)-2,3-dihydro-9-hydroxy-p-dioxino [2,3-g] quinoline-8-carboxylic acid ethyl ester and salts thereof with pharmaceutically acceptable acids.

31. The diuretic composition of claim 1 wherein the compound is a member selected from the group consisting of 3-(acetoxymethyl)-2,3-dihydro-9-hydroxy-p-dioxino [2,3-g] quinoline-8-carboxylic acid ethyl ester and salts thereof with pharmaceutically acceptable acids.

32. The diuretic composition of claim 1 wherein the compound is a member selected from the group consisting of 3-(ethoxymethyl)-2,3-dihydro-9-hydroxy-10-methyl-p-dioxino [2,3-g] quinoline-8-carboxylic acid ethyl ester and salts thereof with pharmaceutically acceptable acids.

33. The diuretic composition of claim 1 wherein the compound is a member selected from the group consisting of 3-(ethoxymethyl)-2,3-dihydro-9-hydroxy-10-methoxy-p-dioxino [2,3-g] quinoline-8-carboxylic acid ethyl ester and salts thereof with pharmaceutically acceptable acids.

34. The diuretic composition of claim 1 wherein the compound is a member selected from the group consisting of 3-(ethoxymethyl)-2,3-dihydro-9-hydroxy-p-dioxino [2,3-g] quinoline-8-carboxylic acid methyl ester and salts thereof with pharmaceutically acceptable acids.

35. The diuretic composition of claim 1 wherein the compound is a member selected from the group consisting of 3-(ethoxymethyl)-2,3-dihydro-9-hydroxy-p-dioxino [2,3-g] quinoline-8-carboxyl acid isobutyl ester and salts thereof with pharmaceutically acceptable acids.

36. A method of treating a patient sufeering from edema comprising administering to said patient an effective dosage of the diuretic composition of claim 1.

* * * * *